US00PP09922P

United States Patent [19]

Rabin

[11] Patent Number: Plant 9,922

[45] Date of Patent: Jun. 10, 1997

[54] GUZMANIA PLANT NAMED 'SCARLET KNIGHT'

[75] Inventor: Mitch Rabin, Goulds, Fla.

[73] Assignee: Twyford International, Inc., Santa Paula, Calif.

[21] Appl. No.: 597,042

[22] Filed: Feb. 5, 1996

[51] Int. Cl.[6] ..... A01H 5/00

[52] U.S. Cl. ..... Plt./88.8

[58] Field of Search ..... Plt./88.8

*Primary Examiner*—James R. Feyrer

*Attorney, Agent, or Firm*—Foley & Lardner

[57] ABSTRACT

A new cultivar of Guzmania named 'Scarlet Knight', having a large, broad, compact, clean, long-lasting, red-orange inflorescence with yellow tipped terminal bracts.

3 Drawing Sheets

1

The present invention relates to a new and distinct cultivar of Guzmania, a genus within the family bromeliaceae, hereinafter referred by the cultivar name 'Scarlet Knight'. The new cultivar is an unusual selection discovered among a group of F1 Hybrid Guzmania 'Cherry' grown from seeds.

Guzmania comprise a genus of over 100 species of evergreen perennials suitable for cultivation in the home or under glass. Guzmania are predominantly epiphytic with a few terrestrial species and are native to the tropics. For the most part the species vary in diameter from 7 to 8 inches to 3 or 4 feet and have rosettes of glossy, smooth edged leaves.

Floral bracts of Guzmania frequently have brilliant colors and may last for many months. The range of flower colors for Guzmania is generally from yellow through orange but may also include flame red and red-purple. White or yellow, tubular, three petalled flowers may also appear on a stem or within the leaf rosette but are usually short lived.

Guzmania may be advantageously grown as pot plants for greenhouse or home use. Desirably the plants are shaded from direct sunlight and during the spring to autumn period, the central vase-like part of the leaf rosette is normally filled with water.

Guzmania is native to tropical America. Leaves of the Guzmania are usually formed as basal rosettes which are stiff and entire and in several vertical ranks. Guzmania have terminal spikes or panicles which are often bracted, bearing flowers with petals united in a tube about as long as the calyx.

Asexual propagation of Guzmania is frequently done through the use of tissue culture practices. Propagation can also be from off-shoots produced by the plant which may then be rooted. The resulting off-shoots are detached from the mother plant and may be grown in an appropriate soil or bark mixture. Many types are propagated relatively uniformly from seeds.

The new cultivar 'Scarlet Knight' was discovered by inventor Mitch Rabin in Goulds, Fla. growing among a group of seed derived F1 Hybrid Guzmania 'Cherry', an unpatented cultivar. The selection comprising the new cultivar was chosen after commencement of flowering in August 1989, being recognized for its unusual inflorescence. Subsequent asexual propagation of 'Scarlet Knight' by off-shoots by the inventor in Goulds, Fla. has demonstrated that the combination of characteristics as herein disclosed for 'Scarlet Knight' are firmly fixed and are retained through successive generations of asexual reproduction.

The following traits have been repeatedly observed to be characteristics which in combination distinguish 'Scarlet Knight' from known cultivars and from 'Cherry', the closest comparison cultivar and to which reference is made. 'Cherry' is known for its tall, red-orange, long lasting inflorescence, and dark green glossy foliage.

2

1. The inflorescence produced by 'Scarlet Knight' is much broader, and shorter than that of 'Cherry'.

2. 'Scarlet Knight' has bright red-orange bracts with contrasting yellow tipped terminal bracts.

3. Vestigial and functional flowers are present in the terminal part of the spike, and in lateral branch spikes. However, the flowers seldom emerge completely from under the bracts.

4. Because the flowers are few, and only partially emerge from under the bracts, the inflorescence is cleaner appearing and longer lasting. The inflorescence does not appear "flowered-out" with age.

'Scarlet Knight' has not been tested under all available environmental conditions, and the phenotype may vary with variations in environmental conditions such as temperature, light intensity, day length and humidity without, however, any variance in genotype.

The accompanying color photographic drawings show typical characteristics of 'Scarlet Knight', with colors being as true as possible with illustrations of this type.

The photograph on sheet 1 illustrates a 12-month old plant of 'Scarlet Knight' grown from an off-shoot, and finished in a 15.5 cm pot.

The photograph on sheet 2 is a close up view showing details of an inflorescence of 'Scarlet Knight'.

The photograph on sheet 3 is a comparison of similar age plants of 'Scarlet Knight' and 'Cherry' grown in the same location. 'Scarlet Knight' is on the left and 'Cherry' is on the right.

The following description is based on the plant of 'Scarlet Knight' illustrated in the photographs on sheets 1 and 2. The plant was grown in Goulds, Fla. by the inventor in shade-house conditions which are typical of the industry. Color references are made to The Royal Horticultural Society Colour Chart (R.H.S.).

Plant:

*Form/growth habit.*—Basal Rosette of strap-like leaves arranged around a central axis.

*Height.*—Approximately 43 cm including inflorescence.

*Diameter.*—Approximately 65 cm–70 cm.

Foliage:

*Size of leaf.*—The basal leaves are approximately 38 cm–44 cm long, and 3.5 cm–4.5 cm wide.

*Shape of leaf.*—The leaf blade is ligulate with an acute apiculate tip. The surface is flat or slightly channeled. The margins are entire.

*Surface texture.*—The leaf blade is thin, coriaceous, smooth and glossy.

*Color.*—The leaves are medium green throughout the foliage. The adaxial surface is darker and greener than but closest to 137 A, and the abaxial surface is greener than but closet to 147 B. the innermost leaf surfaces are lightly flushed with red-purple 59 A.

*Average number of leaves.*—The plant produces approximately 24 leaves before producing an inflorescence.

*Roots.*—Roots white changing to brown, wiry, with fine laterals.

Bracts:

*Size and color.*—The uppermost terminal bracts and those of lateral branch spikes are approximately 4.3 cm–5.5 cm long, approximately 1.0 cm to 1.5 cm wide, and 18 A in color, suffused with 33 B toward the base.

The primary bracts are approximately 14 cm to 16 cm long diminishing to 8 cm to 10 cm long near the terminal, and 3.7 cm to 4.0 cm wide diminishing to 2.5 cm to 3.1 cm wide near the terminal. The adaxial and abaxial surfaces are darker and more orange than, but closest to 33A in color. The tips of the primary bracts are dark anthocyanous 187 A in color. The scape bracts are approximately 25 cm to 30 cm long, and approximately 4.0 cm to 4.7 cm wide, The adaxial surface is 137 A, and the abaxial surface is greener than but closest to 147 B with red-orange 34 B areas where the bract separates from the stem.

*General shape.*—The bracts are ligulate with acute tips, densely imbricate in vertical ranks along the capitate inflorescence.

*Number.*—Terminal Bracts: Approximately 18. Primary Bracts: Approximately 17 to 19. Scape Bracts: Approximately 7.

*Texture.*—Smooth and glossy.

*Margin.*—Entire.

*Scape.*—The scape is approximately 35 cm tall, approximately 9 mm to 13 mm in diameter, and 145 B in color.

Flowers:

*Borne.*—One to three, short 4–6 cm long lateral branches under primary bracts, or terminal in the inflorescence. Lateral branches may be absent or present depending upon the growing conditions.

*Shape of inflorescence.*—The inflorescence is star shaped when viewed from above, terminal in origin, and densely pennate.

*Individual flowers.*—Approximately 30 flower buds present, terminal in the inflorescence concealed under bracts. Calyx: Gamosepalous, three sepals present 2.8 cm long, 0.6 cm wide, translucent 11 D in color. Corolla: Gamopetalous, three petals present, 5.4 cm long, 0.5 cm wide, yellow 13 B in color.

*Time of blooming.*—In mature plants, the inflorescene is in full color approximately 14 weeks after induction, at any time of the year.

*Duration of Inflorescence.*—The inflorescence will hold its color approximately 4 to 6 months.

Reproductive Organs:

*Ovary.*—Superior, three locules, 11 mm long, 4 mm wide, 150 D in color.

*Style.*—4.1 cm long, 0.8 mm wide, 150 D in color.

*Stamens.*—Six present, filament 4 cm long, anthers 8 mm long, yellow 11 D in color.

Seed Characteristics: Sterile F1 hybrid.

I claim:

1. A new and distinct cultivar of Guzmania plant named 'Scarlet Knight', as illustrated and described.

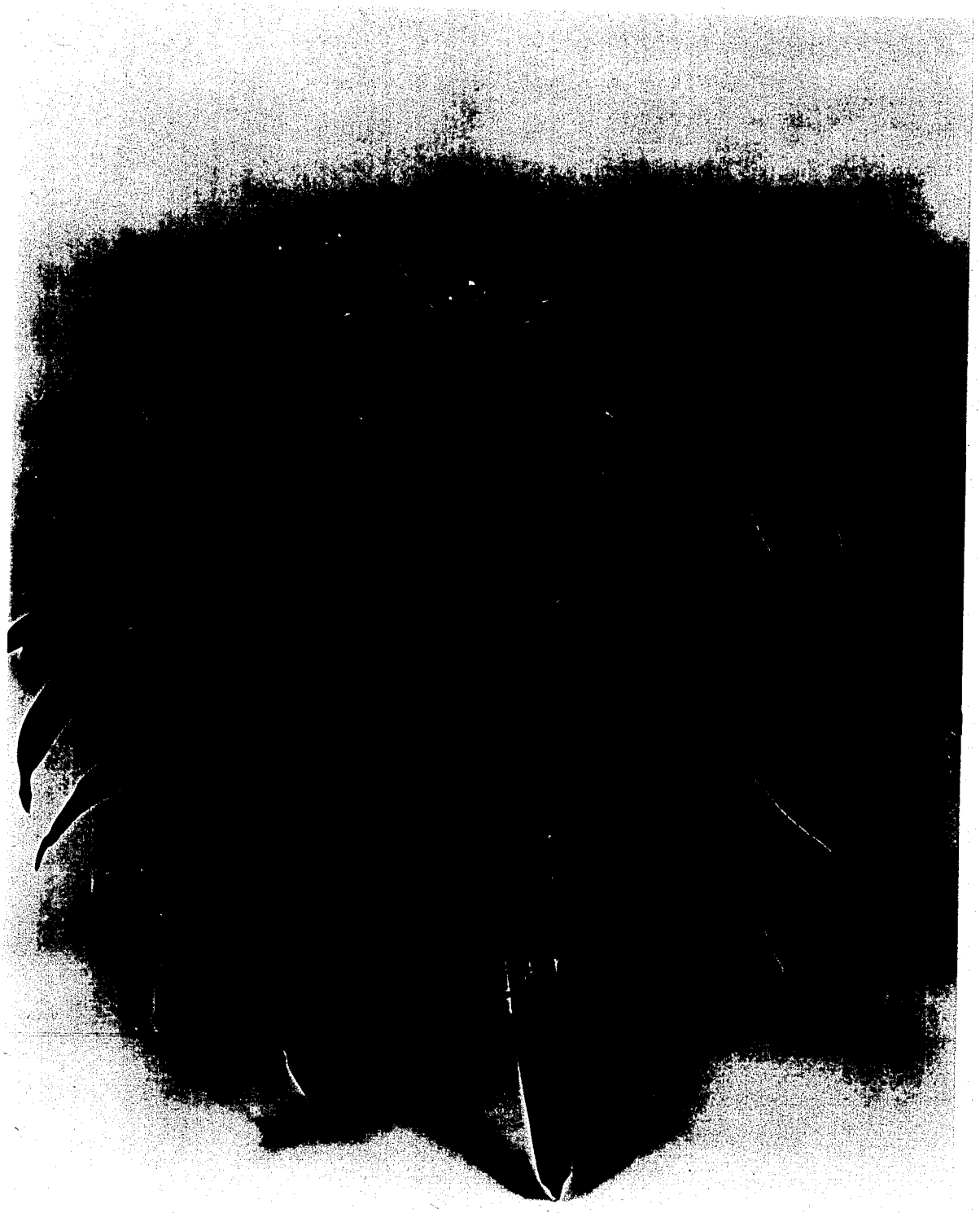

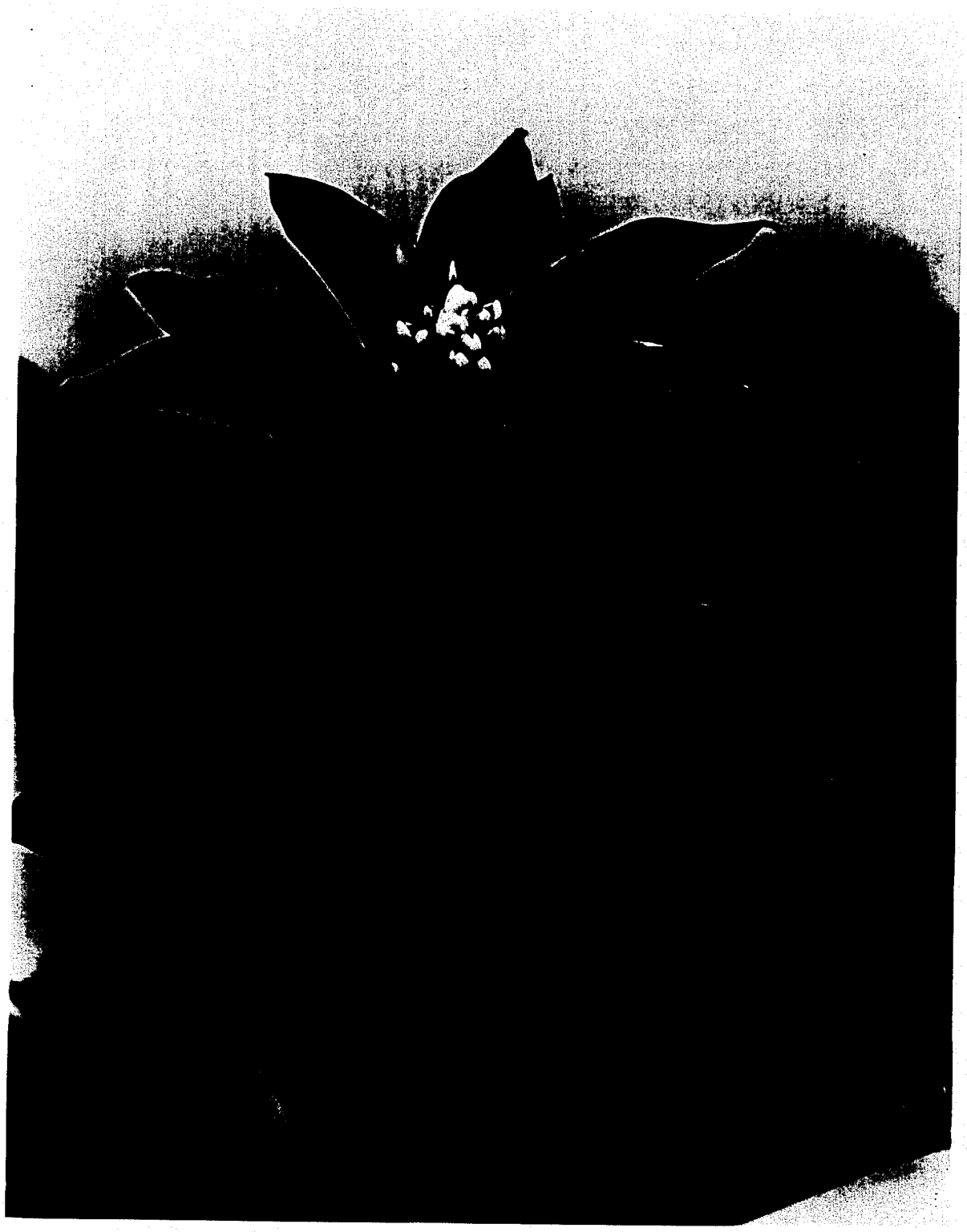

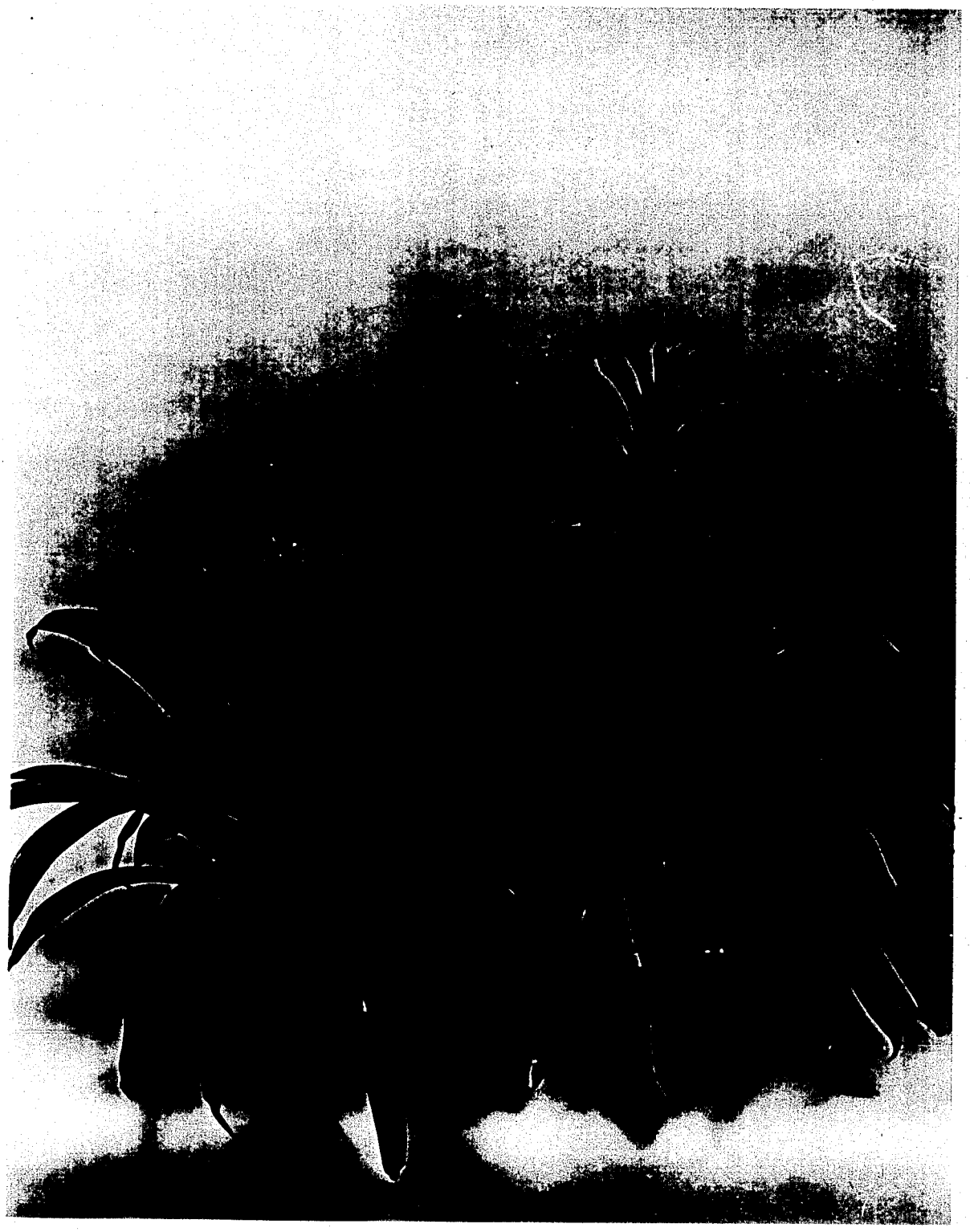

* * * * *